US011554109B2

(12) United States Patent
Oshima et al.

(10) Patent No.: US 11,554,109 B2
(45) Date of Patent: Jan. 17, 2023

(54) PEMAFIBRATE DOSING REGIMENS

(71) Applicant: Kowa Company, Ltd.

(72) Inventors: Ryu Oshima, Chuo-ku (JP); Masatoshi Ito, Chuo-ku (JP); Chisato Nagai, Chuo-ku (JP)

(73) Assignee: Kowa Company, Ltd.

( * ) Notice: Subject to any disclaimer, the term of this patent is extended or adjusted under 35 U.S.C. 154(b) by 0 days.

(21) Appl. No.: 17/708,706

(22) Filed: Mar. 30, 2022

(65) Prior Publication Data

US 2022/0296588 A1    Sep. 22, 2022

Related U.S. Application Data

(63) Continuation of application No. 16/626,748, filed as application No. PCT/JP2018/024954 on Jun. 29, 2018, now abandoned.

(30) Foreign Application Priority Data

Jun. 30, 2017 (JP) .................................. 2017-128188

(51) Int. Cl.
| | |
|---|---|
| *A61K 31/423* | (2006.01) |
| *A61K 31/34* | (2006.01) |
| *A61K 31/4152* | (2006.01) |
| *A61K 31/427* | (2006.01) |
| *A61K 31/4353* | (2006.01) |
| *A61K 31/4402* | (2006.01) |
| *A61K 31/4433* | (2006.01) |
| *A61K 31/4709* | (2006.01) |
| *A61K 31/496* | (2006.01) |
| *A61K 31/513* | (2006.01) |
| *A61K 31/7034* | (2006.01) |
| *A61K 38/13* | (2006.01) |
| *A61P 3/06* | (2006.01) |
| *A61K 31/7048* | (2006.01) |
| *A61K 45/06* | (2006.01) |

(52) U.S. Cl.
CPC ............ *A61K 31/423* (2013.01); *A61K 31/34* (2013.01); *A61K 31/4152* (2013.01); *A61K 31/427* (2013.01); *A61K 31/4353* (2013.01); *A61K 31/4402* (2013.01); *A61K 31/4433* (2013.01); *A61K 31/4709* (2013.01); *A61K 31/496* (2013.01); *A61K 31/513* (2013.01); *A61K 31/7034* (2013.01); *A61K 31/7048* (2013.01); *A61K 38/13* (2013.01); *A61P 3/06* (2018.01); *A61K 45/06* (2013.01)

(58) Field of Classification Search
None
See application file for complete search history.

(56) References Cited

U.S. PATENT DOCUMENTS

| | | | |
|---|---|---|---|
| 4,847,265 A | 7/1989 | Badorc et al. | |
| 11,298,340 B2* | 4/2022 | Sugimoto | ................. A61P 3/06 |
| 11,419,854 B2* | 8/2022 | Kojima | ................ A61K 31/423 |
| 11,446,282 B2* | 9/2022 | Oshima | ...................... A61P 3/06 |
| 2005/0101636 A1 | 5/2005 | Yamazaki et al. | |
| 2006/0189667 A1 | 8/2006 | Yamazaki et al. | |
| 2014/0234317 A1 | 8/2014 | Onsum et al. | |
| 2022/0257627 A1* | 8/2022 | Oshima | .............. A61K 31/4709 |

FOREIGN PATENT DOCUMENTS

| | | |
|---|---|---|
| JP | 6-45622 B2 | 6/1994 |
| JP | 2014-514359 A | 6/2014 |
| WO | WO 2005/023777 A1 | 3/2005 |

OTHER PUBLICATIONS

Ogawa et al., "Plasma concentrations of pemafibrate with coadministered drugs predicted by physiologically based pharmacokinetic modeling in virtual populations with renal/hepatic impairment", Jan. 2020, Xenobiotica, 50:9, pp. 1023-1031. (DOI: 10.1080/00498254.2019.1709133) (Year: 2020).*

Ogawa et al., "Increased plasma concentrations of an antidyslipidemic drug pemafibrate co-administered with rifampicin or cyclosporine A in cynomolgus monkeys genotyped for the organic anion transporting polypeptide 1 B1", Apr. 2020, 35(4), pp. 354-360. (doi.org/10.1016/j.dmpk.2020.03.005) (Year: 2020).*

Park et al., "Improved Prediction of the Drug-Drug Interactions of Pemafibrate Caused by Cyclosporine A and Rifampicin via PBPK Modeling: . . . Against OATP1B", 2021, Journal of Pharmaceutical Sciences, 110(1), pp. 517-528. (doi.org/10.1016/j.xphs.2020.10.016) (Year: 2021).*

International Search Report dated Jul. 31, 2018 in PCT/JP2018/024954 filed on Jun. 29, 2018, 6 pages.

Ishibashi, et al., "Effects of K-877, a novel selective PPARα modulator (SPPARMα), in dyslipidaemic patients: A randomized, double blind, active- and placebo-controlled, phase 2 trial," Atherosclerosis, Jun. 2016, vol. 249, pp. 36-43.

Kowa Research Institute, Inc., Drug-Drug Interaction Study in Healthy Adult Volunteers, clinical trial "NCT02275962" registered on clinicaltrials.gov, Feb. 1, 2016, Study Details column, [retrieved on Jul. 17, 2016] retrieved from the internet: <URL: https://clinicaltrials.gov/ct2/show/NCT02275962> (total 4 pages).

(Continued)

*Primary Examiner* — My-Chau T. Tran
(74) *Attorney, Agent, or Firm* — Clark Sullivan

(57) ABSTRACT

To provide a medicament for safely treating a patient in need of treatment with pemafibrate, a salt thereof, or a solvate of any of these (hereinafter also referred to as pemafibrate therapy).

A medicament for treating a patient in need of pemafibrate therapy, the medicament comprising the step of avoiding or suspending concomitant use of pemafibrate, a salt thereof, or a solvate of any of these as an active ingredient in order to suppress an increase in plasma concentration of pemafibrate when the treatment is combined with a medicament containing an OATP1B inhibitor, or the step of reducing the dose of pemafibrate, a salt thereof, or a solvate of any of these.

6 Claims, No Drawings

(56) References Cited

OTHER PUBLICATIONS

Kowa Research Institute, Inc., Drug-Drug Interaction Study its Healthy Adult Volunteers, clinical trial "NCT02275988" registered on clinicaltrials.gov, Oct. 27, 2014. Study Details column, [retrieved on Jul. 17, 2018] retrieved from the internet: <URL: https://clinicaltrials.gov/ct2/show/NCT02275988> (total 4 pages).

Kowa Research Institute, Inc., Drug-Drug Interaction Study in Healthy Adult Volunteers, clinical trial "NCT02276001" registered on clinicaltrials.gov, Oct. 27, 2014, Study Details column, [retrieved on Jul. 17, 2018] retrieved from the internet: <URL: https://clinicaltrials.gov/ct2/show/NCT02276001> (total 4 pages).

Kowa Research Institute, Inc., Drug-Drug Interaction Study in Healthy Adult Volunteers, clinical trial "NCT02922465" registered on clinicaltrials.gov, Dec. 21, 2016, Study Details column, [retrieved on Jul. 17, 2018] retrieved from the internet: <URL: https://clinicaltrials.gov/ct2/show/NCT02922465> (total 4 pages).

Harashima, "New Pharmacology," Third Revised Edition, Nankodo Co., Ltd., 2011, pp. 268-269 (total 4 pages).

"Office Communication: Guidelines for Pharmacokinetic Drug Interaction for Drug Development and Proper Information Provision (Final Draft)," Ministry of Health, Labour and Welfare, Pharmaceutical and Food Safety Bereau, Evaluation and Licensing Division, Jul. 8, 2014 (total 80 pages).

Baba, et al., "Combination Therapy Using Pemafibrate: Drug Interactions," Progress in Medicine, Sep. 2017, vol. 37, No. 9, pp. 1051-1054 (with concise explanation in English), (total 5 pages).

\* cited by examiner

PEMAFIBRATE DOSING REGIMENS

TECHNICAL FIELD

The present invention relates to a new medicament for efficient and safe use of pemafibrate, a salt thereof, or a solvate of any of these.

BACKGROUND ART

Pemafibrate (Chemical name: (2R)-2-[3-({1,3-benzoxazol-2-yl[3-(4-methoxyphenoxy) propyl]amino}methyl)phenoxy]butanoic acid), a salt thereof, or a solvate of any of these are compounds having PPARα activity and are known to be useful for the prevention and/or treatment of diseases such as dyslipidemia (Patent Literature 1).

Rifampicin (2S, 12Z, 14E, 16S, 17S, 18R, 19R, 20R, 21S, 22R, 23S, 24E)5,6,9,17,19-pentahydroxy-23-methoxy-2,4,12,20,22-heptamethyl-8-(4-methylpiperazin-1-yliminomethyl)1,11-dioxo-1,2-dihydro-7-(epoxypentadeca[1,11,13] trienimino)[2,1-b]furan-21yl acetate is an organic compound represented by the following formula (1)

[Formula 1]

which is an antibiotic listed in the WHO-Essential Drug Model List (WHO Model List of Essential Medicines, 19th List).

Clarithromycin is a compound represented by the following formula (2)

[Formula 2]

which is an antibiotic listed in the WHO-Essential Drug Model List (WHO Model List of Essential Medicines, 19th List).

Cyclosporine is an immunosuppressive agent used to suppress rejection in the organ transplantation of kidneys, liver, heart or bone-marrow and to treat graft-versus-host diseases, which is listed in the WHO-Essential Drug Model List (WHO Model List of Essential Medicines, 19th List).

Clopidogrel (Chemical Name: methyl (2S)-2-(2-chlorophenyl)-2-[6,7-dihydrothieno[3,2-c]pyridin-5(4H)-yl]acetate), a salt thereof, or a solvate of any of these are compounds known to have platelet aggregation inhibitory and antithrombotic activities (Patent Literature 2).

Multiple drugs are often prescribed for therapeutic purposes in the clinical practice, and attention should be paid to interactions between the drugs used concomitantly. Because drug interactions may cause serious side effects and/or diminish therapeutic effects, the property and extent of potential drug interactions should be adequately assessed and addressed in the development of new drugs so that they do not pose a disadvantage to the patients.

PRIOR ART DOCUMENTS

Patent Literature

[Patent Literature 1] WO 2005/023777 pamphlet
[Patent Literature 2] JP-B-Hei 6-45622

SUMMARY OF THE INVENTION

Problems to be Solved by the Invention

The pharmacokinetics of pemafibrate, a salt thereof, or a solvate of any of these and their interactions with other drugs are not described in the above Prior art Documents.

The present invention addresses to provide a medicament for safe treatment of a patient in need of treatment with pemafibrate, a salt thereof, or a solvate of any of these (hereinafter also referred to as pemafibrate therapy).

Means for Solving the Problem

In order to solve the above problems, the present inventors conducted extensive researches, and as a result, the present inventors have found that caution should be exercised when pemafibrate is used concomitantly with rifampicin because of the rise in the plasma concentration of pemafibrate. We also found that the interaction caused by the concomitant use of pemafibrate with rifampicin was due to the fact that rifampicin is an inhibitor of organic anion-transporting polypeptides (OATP1B), which is a hepatic uptake transporter. The present inventors have found that a patient in need of treatment with pemafibrate, a salt thereof, or a solvate of any of these can be safely treated by avoiding or suspending the concomitant use of pemafibrate with an OATP1B inhibitor such as rifampicin, or by reducing the dose of pemafibrate, a salt thereof, or a solvate of any of these, and the present invention has been completed.

In addition, it was found that concomitant use of pemafibrate with clarithromycin, cyclosporine, or clopidogrel also increased the plasma concentration of pemafibrate, requiring caution when concomitantly used.

The present invention also found that the combined interaction of pemafibrate with clarithromycin, cyclosporine, or clopidogrel was due to clarithromycin, cyclosporine, or clopidogrel being a drug that inhibits OATP1B and further inhibits the action of certain cytochrome P450 (CYPs). The present inventors have found that a patient in need of treatment with pemafibrate a salt thereof, or a solvate of any of these can be safely treated by avoiding or suspending the concomitant use of pemafibrate with an OATP1B inhibitor and/or a CYP inhibitor, or by reducing the dose of pemafibrate, a salt thereof, or a solvate of any of these, and the present invention has been completed.

The present invention provides the following [1] to [58].

[1] A medicament comprising pemafibrate, a salt thereof, or a solvate of any of these as an active ingredient, for use in the treatment of a patient in need of pemafibrate therapy, in order to suppress an increase in plasma concentration of pemafibrate when the treatment is concomitant use of pemafibrate with a medicament comprising an OATP1B inhibitor, the medicament comprising a step of avoiding or suspending the concomitant use or a step of reducing the dose of pemafibrate, a salt thereof, or a solvate of any of these.

[2] The medicament according to [1], wherein the pemafibrate, a salt thereof, or a solvate of any of these is pemafibrate.

[3] The medicament according to [1] or [2], wherein the OATP1B inhibitor is one or more drugs selected from the group consisting of clarithromycin, rifampicin, cyclosporine, a combination agent of lopinavir and ritonavir, a combination agent of atazanavir and ritonavir, a combination agent of dalnavir and ritonavir, clopidogrel, eltrombopag, a combination agent of saquinavir and ritonavir, a combination agent of tipranavir and ritonavir, and gemfibrozil.

[4] The medicament according to any one of [1] to [3], wherein the patient in need of pemafibrate therapy is a patient with one or more diseases selected from the group consisting of hyperlipidemia, dyslipidemia, arteriosclerosis, diabetes mellitus, diabetic complications, inflammation, non-alcoholic steatohepatitis, primary biliary cirrhosis, and heart disease.

[5] The medicament according to any one of [1] to [4], wherein the patient is a patient further in need of pemafibrate therapy during treatment with an OATP1B inhibitor.

[6] The medicament according to any one of [1] to [4], wherein the patient is a patient further in need of treatment with an OATP1B inhibitor during pemafibrate therapy.

[7] The medicament according to any one of [1] to [6], wherein the step of reducing the dose of pemafibrate, a salt thereof, or a solvate of any of these is to reduce the dose of pemafibrate, a salt thereof, or a solvate of any of these, compared with the dose when the drug is administered alone, to ½ or less.

[8] The medicament according to any one of [1] to [7], wherein the step of reducing the dose of pemafibrate, a salt thereof, or a solvate of any of these is to set the dose of pemafibrate, a salt thereof, or a solvate of any of these as 0.1 to 0.2 mg/day.

[9] The medicament according to any one of [1] to [8], wherein the pemafibrate, a salt thereof, or a solvate of any of these is administered twice per day.

[10] A pharmaceutical kit comprising (A) a medicament comprising pemafibrate, a salt thereof, or a solvate of any of these as an active ingredient; and (B) an instruction to avoid or suspend concomitant use of the (A) with a medicament comprising an OATP1B inhibitor, or to reduce the dose of pemafibrate, a salt thereof, or a solvate of any of these at the time of the concomitant use.

[11] The pharmaceutical kit according to [10], wherein the pemafibrate, a salt thereof, or a solvate of any of these is pemafibrate.

[12] The pharmaceutical kit according to [10] or [11], wherein the OATP1B inhibitor is one or more drugs selected from the group consisting of clarithromycin, rifampicin, cyclosporine, a combination agent of lopinavir and ritonavir, a combination agent of atazanavir and ritonavir, a combination agent of dalnavir and ritonavir, clopidogrel, eltrombopag, a combination agent of saquinavir and ritonavir, a combination agent of tipranavir and ritonavir, and gemfibrozil.

[13] The pharmaceutical kit according to anyone of [10] to [12], wherein the medicament of (A) is a drug for the prevention and/or treatment for one or more diseases selected from the group consisting of hyperlipidemia, dyslipidemia, arteriosclerosis, diabetes mellitus, diabetic complications, inflammation, non-alcoholic steatohepatitis, primary biliary cirrhosis, and heart disease.

[14] The pharmaceutical kit according to any one of [10] to [13], instructing to reduce the dose of pemafibrate, a salt thereof, or a solvate of any of these, compared with the dose when the drug is administered alone, to ½ or less.

[15] The pharmaceutical kit according to any one of [10] to [14], instructing to set the dose of pemafibrate, a salt thereof, or a solvate of any of these as 0.1 to 0.2 mg per day.

[16] The pharmaceutical kit according to any one of [10] to [15], instructing to administer pemafibrate, a salt thereof, or a solvate of any of these twice per day.

[17] The pharmaceutical kit according to any one of [10] to [16], wherein the instruction is a package insert, a package label, or a user manual.

[18] A medicament comprising pemafibrate, a salt thereof, or a solvate of any of these as an active ingredient, for use in the treatment of a patient in need of pemafibrate therapy, in order to suppress an increase in plasma concentration of pemafibrate when the treatment is concomitant use of pemafibrate with a medicament comprising a CYP inhibitor, the medicament comprising a step of avoiding or suspending the concomitant use or a step of reducing the dose of pemafibrate, a salt thereof, or a solvate of any of these.

[19] The medicament according to [18], wherein the pemafibrate, a salt thereof, or a solvate of any of these is pemafibrate.

[20] The medicament according to [18] or [19], wherein the CYP inhibitor is a drug that inhibits CYP3A.

[21] The medicament according to [20], wherein the drug that inhibits CYP3A is one or more drugs selected from the group consisting of clarithromycin, cyclosporine, cobicistat, indinavir, itraconazole, ritonavir, telaprevir, voriconazole, nelfinavir, saquinavir, boceprevir, conivaptan, ketoconazole, a combination agent of lopinavir and ritonavir, mibefradil, nefazodone, posaconazole, telithromycin, fluconazole, amprenavir, aprepitant, atazanavir, ciprofloxacin, crizotinib, a combination agent of darnavir and ritonavir, diltiazem, erythromycin, fosamprenavir, imatinib, istradefylline, miconazole, tofisopam, casopitant, dronedarone, and verapamil.

[22] The medicament according to [18] or [19], wherein the CYP inhibitor is a drug that inhibits CYP2C8.

[23] The medicament according to [22], wherein the drug that inhibits CYP2C8 is one or more drugs selected from the group consisting of gemfibrozil, clopidogrel, cyclosporine, deferasirox, and teriflunomide.

[24] The medicament according to [18] or [19], wherein the CYP inhibitor is a drug that inhibits CYP2C9.

[25] The medicament according to [24], wherein the drug that inhibits CYP2C9 is one or more drugs selected from the group consisting of a fluorouracil derivative, carmofur, sulfaphenazole, amiodarone, bucolome, cyclosporine, fluconazole, miconazole, and oxandrolone.

[26] The medicament according to any one of [19] to [25], wherein the patient in need of pemafibrate therapy is a patient with one or more diseases selected from the group consisting of hyperlipemia, dyslipidemia, arteriosclerosis, diabetes mellitus, diabetic complications, inflammation, non-alcoholic steatohepatitis, primary biliary cirrhosis, and heart disease.

[27] The medicament according to any one of [19] to [26], wherein the patient is a patient further in need of pemafibrate therapy during treatment with a CYP inhibitor.

[28] The medicament according to any of [19] to [26], wherein the patient is a patient further in need of treatment with a CYP inhibitor during pemafibrate therapy.

[29] The medicament according to any one of [19] to [28], wherein the step of reducing the dose of pemafibrate, a salt thereof, or a solvate of any of these is to reduce the dose of pemafibrate, a salt thereof, or a solvate of any of these, compared with the dose when the drug is administered alone, to ½ or less.

[30] The medicament according to any one of [19] to [29], wherein the step of reducing the dose of pemafibrate, a salt thereof, or a solvate of any of these is to set the dose of pemafibrate, a salt thereof, or a solvate of any of these as 0.1 to 0.2 mg/day.

[31] The medicament according to any one of [19] to [30], wherein the pemafibrate, a salt thereof, or a solvate of any of these is administered twice per day.

[32] The medicament according to any one of [19] to [31], wherein the CYP inhibitor is a drug that further inhibits OATP1B.

[33] A pharmaceutical kit comprising (A) a medicament comprising pemafibrate, a salt thereof, or a solvate of any of these as an active ingredient; and (B) an instruction to avoid or suspend concomitant use of the (A) with a medicament comprising a CYP inhibitor, or to reduce the dose of pemafibrate, a salt thereof, or a solvate of any of these at the time of the concomitant use.

[34] The pharmaceutical kit according to [33], wherein the pemafibrate, a salt thereof, or a solvate of any of these is pemafibrate.

[35] The pharmaceutical kit according to [33] or [34], wherein the CYP inhibitor is a drug that inhibits CYP3A.

[36] The pharmaceutical kit according to [35], wherein the drug that inhibits CYP3A is one or more drugs selected from the group consisting of clarithromycin, cyclosporine, cobicistat, indinavir, itraconazole, ritonavir, telaprevir, voriconazole, nelfinavir, saquinavir, boceprevir, conivaptan, ketoconazole, a combination agent of lopinavir and ritonavir, mibefradil, nefazodone, posaconazole, telithromycin, fluconazole, amprenavir, aprepitant, atazanavir, ciprofloxacin, crizotinib, a combination agent of darnavir and ritonavir, diltiazem, erythromycin, fosanprenavir, imatinib, istradefylline, miconazole, tofisopam, casopitant, dronedarone, and verapamil.

[37] The pharmaceutical kit according to [33] or [34], wherein the CYP inhibitor is a drug that inhibits CYP2C8.

[38] The pharmaceutical kit according to (37), wherein the drug that inhibits CYP2C8 is one or more drugs selected from the group consisting of gemfibrozil, clopidogrel, cyclosporine, deferasirox, and teriflunomide.

[39] The pharmaceutical kit according to [33] or [34], wherein the CYP inhibitor is a drug that inhibits CYP2C9.

[40] The pharmaceutical kit according to [39], wherein the drug that inhibits CYP2C9 is one or more drugs selected from the group consisting of a fluorouracil derivative, carmofur, sulfaphenazole, amiodarone, bucolome, cyclosporine, fluconazole, miconazole, and oxandrolone.

[41] The pharmaceutical kit according to any one of [33] to [40], wherein the medicament of (A) is a drug for the prevention and/or treatment for one or more diseases selected from the group consisting of hyperlipidemia, dyslipidemia, arteriosclerosis, diabetes mellitus, diabetic complications, inflammation, non-alcoholic steatohepatitis, primary biliary cirrhosis, and heart disease.

[42] The pharmaceutical kit according to any one of [33] to [41], instructing to reduce the dose of pemafibrate, a salt thereof, or a solvate of any of these, compared with the dose when the drug is administered alone, to ½ or less.

[43] The pharmaceutical kit according to any one of [33] to [42], instructing to set the dose of pemafibrate, a salt thereof, or a solvate of any of these as 0.1 to 0.2 mg per day.

[44] The pharmaceutical kit according to any one of [33] to [43], instructing to administer pemafibrate, a salt thereof, or a solvate of any of these twice per day.

[45] The pharmaceutical kit according to any one of [33] to [44], wherein the instruction is a package insert, a package label, or a user manual.

[46] The pharmaceutical kit according to anyone of [33] to [45], wherein the CYP inhibitor is a drug that further inhibits OATP1B.

[47] A medicament comprising pemafibrate, a salt thereof, or a solvate of any of these as an active ingredient, for use in the treatment of a patient in need of pemafibrate therapy, in order to suppress an increase in plasma concentration of pemafibrate when the treatment is concomitant use of pemafibrate with a medicament comprising an OATP1B inhibitor, comprising an optional step of avoiding or suspending the concomitant use or reducing the dose of pemafibrate, a salt thereof, or a solvate of any of these.

[48] A pharmaceutical kit comprising (A) a medicament comprising pemafibrate, a salt thereof, or a solvate of any of these as an active ingredient; and (B) an instruction optionally to avoid or suspend concomitant use of the (A) with a medicament comprising an OATP1B inhibitor, or to reduce the dose of pemafibrate, a salt thereof, or a solvate of any of these at the time of the concomitant use.

[49] A medicament comprising pemafibrate, a salt thereof, or a solvate of any of these as an active ingredient, for use in the treatment of a patient in need of pemafibrate therapy, in order to suppress an increase in plasma concentration of pemafibrate when the treatment is concomitant use of pemafibrate with a medicament comprising a CYP inhibitor, comprising an optional step of avoiding or suspending the concomitant use or reducing the dose of pemafibrate, a salt thereof, or a solvate of any of these.

[50] A pharmaceutical kit comprising (A) a medicament comprising pemafibrate, a salt thereof, or a solvate of any of these as an active ingredient; and (B) an instruction optionally to avoid or suspend concomitant use of the (A) with a CYP inhibitor, or to reduce the dose of pemafibrate, a salt thereof, or a solvate of any of these at the time of the concomitant use.

[51] A method of treating a patient in need of pemafibrate therapy, comprising a step of avoiding or suspending concomitant use of pemafibrate, a salt thereof, or a solvate of any of these with an OATP1B inhibitor or reducing the dose of pemafibrate, a salt thereof, or a solvate of any of these, in order to suppress an increase in plasma concentration of pemafibrate in the concomitant use.

[52] A method of treating a patient in need of pemafibrate therapy, comprising an optional step of avoiding or suspending concomitant use of pemafibrate, a salt thereof, or a solvate of any of these with an OATP1B inhibitor or reducing the dose of pemafibrate, a salt thereof, or a solvate of any of these, in order to suppress an increase in plasma concentration of pemafibrate in the concomitant use.

[53] Use of pemafibrate, a salt thereof, or a solvate of any of these for treating a patient in need of pemafibrate therapy, comprising a step of avoiding or suspending concomitant use of pemafibrate, a salt thereof, or a solvate of any of these with an OATP1B inhibitor or reducing the dose of pemafibrate, a salt thereof, or a solvate of any of these, in order to suppress an increase in plasma concentration of pemafibrate in the concomitant use.

[54] Use of pemafibrate, a salt thereof, or a solvate of any of these for treating a patient in need of pemafibrate therapy, comprising an optional step of avoiding or suspending concomitant use of pemafibrate, a salt thereof, or a solvate of any of these with an OATP1B inhibitor or reducing the dose of pemafibrate, a salt thereof, or a solvate of any of these, in order to suppress an increase in plasma concentration of pemafibrate in the concomitant use.

[55] A method of treating a patient in need of pemafibrate therapy, comprising a step of avoiding or suspending concomitant use of pemafibrate, a salt thereof, or a solvate of any of these with a CYP inhibitor or reducing the dose of pemafibrate, a salt thereof, or a solvate of any of these, in order to suppress an increase in plasma concentration of pemafibrate in the concomitant use.

[56] A method of treating a patient in need of pemafibrate therapy, comprising an optional step of avoiding or suspending concomitant use of pemafibrate, a salt thereof, or a solvate of any of these with a CYP inhibitor or reducing the dose of pemafibrate, a salt thereof, or a solvate of any of these, in order to suppress an increase in plasma concentration of pemafibrate in the concomitant use.

[57] Use of pemafibrate, a salt thereof, or a solvate of any of these for treating a patient in need of pemafibrate therapy, comprising a step of avoiding or suspending concomitant use of pemafibrate, a salt thereof, or a solvate of any of these with a CYP inhibitor or reducing the dose of pemafibrate, a salt thereof, or a solvate of any of these, in order to suppress an increase in plasma concentration of pemafibrate in the concomitant use.

[58] Use of pemafibrate, a salt thereof, or a solvate of any of these for treating a patient in need of pemafibrate therapy, comprising an optional step of avoiding or suspending concomitant use of pemafibrate, a salt thereof, or a solvate of any of these with a CYP inhibitor or reducing the dose of pemafibrate, a salt thereof, or a solvate of any of these, in order to suppress an increase in plasma concentration of pemafibrate in the concomitant use.

Effect of the Invention

According to the present invention, since an increase in plasma concentration of pemafibrate, a salt thereof, or a solvate of any of these is suppressed, a medicament for effective and safe use can be provided.

DETAILED DESCRIPTION OF THE INVENTION

In the present specification, pemafibrate is a compound represented by the following formula (3)

[Formula 3]

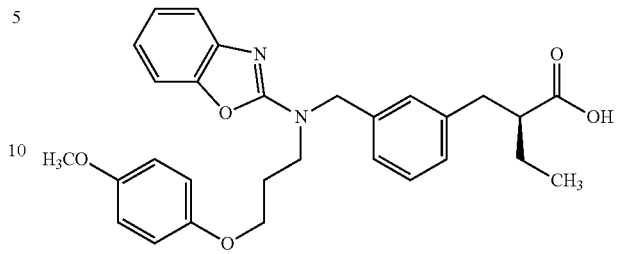

(3)

In the present invention, "pemafibrate, a salt thereof, or a solvate of any of these" includes, in addition to pemafibrate itself, a pharmaceutically acceptable salt of pemafibrate, and a solvate of pemafibrate or a pharmaceutically acceptable salt of pemafibrate with water and the like. In one embodiment of the present invention, the pemafibrate, a salt thereof, or a solvate of any of these is pemafibrate.

Pemafibrate, a salt thereof, or a solvate of any of these can be produced according to the method described in, for example, WO 2005/023777. The compounds may also be formulated according to the methods described in literatures in order to provide them as a medicament.

The medicament containing pemafibrate, a salt thereof, or a solvate of any of these are preferably those for oral administration, and include a tablet, a capsule, a granule and the like.

In the present invention, an "OATP1B inhibitor" is a drug that inhibits the action of organic anion-transporting polypeptides (OATP)1B1 and/or OATP1B3 in the body, examples of which include clarithromycin, rifampicin, cyclosporine, a combination agent of lopinavir and ritonavir, a combination agent of atazanavir and ritonavir, a combination agent of dalnavir and ritonavir, clopidogrel, eltrombopag, a combination agent of saquinavir and ritonavir, a combination agent of tipranavir and ritonavir, and gemfibrozil. It may also be an OATP1B inhibitor as described in the "Drug Interaction Guidelines for Drug Development and Proper Information" (Final Draft), Evaluation and Licensing Division, Pharmaceutical and Food Safety Bureau, MHLW, Jul. 8, 2014, the Guidelines (Guidance for Industry Drug Interaction Studies-Study Design, Data Analysis, Implications for Dosing, and Labeling Recommendations Draft Guidance (February 2012)) of the U.S. Food and Drug Administration, or the Guidelines (Guideline on the investigation of drug interactions (21 Jun. 2012)) of the European Medicines Agency. In one embodiment of the present invention, the OATP1B inhibitor is clarithromycin. In another embodiment of the present invention, the OATP1B inhibitor is rifampicin. In another embodiment of the present invention, the OATP1B inhibitor is cyclosporine. In another embodiment of the present invention, the OATP1B inhibitor is clopidogrel.

Also included in the OATP1B inhibitor are "a drug that inhibits OATP1B1", "a drug that inhibits OATP1B3", and "a drug that inhibits OATP1B1 and OATP1B3." Examples of "a drug that inhibits OATP1B1" include cyclosporine, rifampicin, clarithromycin, a combination agent of lopinavir and ritonavir, combination of atazanavir and ritonavir, a combination agent of dalnavir and ritonavir, a combination agent of saquinavir and ritonavir, gemfibrozil, eltrombopag, a combination agent of tipranavir and ritonavir, and clopidogrel. Examples of "a drug that inhibits OATP1B3" include cyclosporine, rifampicin, clarithromycin, a combination agent of lopinavir and ritonavir, a combination agent of atazanavir and ritonavir, a combination agent of darnavir and ritonavir, a combination agent of saquinavir and ritonavir, and gemfibrozil. Examples of "a drug that inhibit OATP1B1 and OATP1B3" include cyclosporine, rifampicin, clarithromycin, a combination agent of lopinavir and ritonavir, a combination agent of atazanavir and ritonavir, a combination agent of darnavir and ritonavir, a combination agent of saquinavir and ritonavir, and gemfibrozil.

For a medicament containing an OATP1B inhibitor, those for oral administration are preferable, and examples of which include a tablet, a capsule and a granule.

In the present invention, cytochrome P450 or "CYP" are enzymes involved in metabolizing drugs in the liver, and "a CYP inhibitor" refers to a drug that inhibits the action of CYP in the body by ingestion. Examples of "a CYP inhibitor" include, but are not limited to, "a CYP3A inhibitor", "a CYP2C8 inhibitor", and "a CYP2C9 inhibitor." Examples of a drug that inhibits CYP3A include clarithromycin, cyclosporine, cobicystat, indinavir, itraconazole, ritonavir, telaprevir, voriconazole, nelfinavir, saquinavir, boceprevir, conibaptan, ketoconazole, a combination agent of lopinavir and ritonavir, mibefradil, nefazodone, posaconazole, telithromycin, fluconazole, amprenavir, aprepitant, atazanavir, ciprofloxacin, crizotinib, a combination agent of darunavir and ritonavir, diltiazem, erythromycin, fosamprenavir, imatinib, istradefillyne, miconazole, tofisopam, casopitant, dronedarone, and verapamil. Examples of "a drug that inhibits CYP2C8" include gemfibrozil, clopidogrel, cyclosporine, deferasirox, and teriflunomide. Examples of "a drug that inhibits CYP2C9" include fluorouracil derivatives, carmofur, sulfaphenazole, amiodarone, bucolome, cyclosporine, fluconazole, miconazole, and oxandrolone.

The "CYP inhibitor" may be a "drug that inhibits CYP3A", "a drug that inhibits CYP2C8", or "a drug that inhibits CYP2C9" as described in the "Drug Interaction Guideline for Drug Development and Proper Information (Final Draft) (Evaluation and Licensing Division, Pharmaceutical and Food Safety Bureau, MHLW, Jul. 8, 2014), the guideline (Guidance for Industry Drug Interaction Studies-Study Design, Data Analysis, Implications for Dosing, and Labeling Recommendations Draft Guidance (February 2012)) of the U.S. Food and Drug Administration, or the guideline (Guideline on the investigation of drug interactions (21 Jun. 2012)) of the European Medicines Agency.

With respect to CYP enzymes, the U.S. Food and Drug Administration generally defines a "potent inhibitor" as an inhibitor that, in clinical evaluation, caused a >5-fold increase in plasma AUC values or a >80% decrease in clearance of CYP substrates (not limited to sensitive CYP substrates). The U.S. Food and Drug Administration generally defines a "moderate inhibitor" as an inhibitor that, in clinical evaluation, caused a >2-fold increase in AUC values, but a <5-fold increase in clearance of sensitive CYP substrates or a 50% to 80% decrease in clearance of sensitive CYP substrates when the inhibitor was given at the highest approved dose and at the shortest dosing interval. Among the CYP3A inhibitors listed in the above U.S. Food and Drug Administration guidelines, potent CYP3A inhibitors include boceprevir, clarithromycin, conivaptan, indinavir, itraconazole, ketoconazole, a combination agent of lopinavir and ritonavir, mibefradil, nefazodone, nelfinavir, posaconazole, ritonavir, saquinavir, telaprevir, voriconazole; moderate CYP3A inhibitors include amprenavir, aprepitant, atazanavir, ciprofloxacin, crizotinib, a combination agent of darnavir and ritonavir, diltiazem, erythromycin, fluconazole, fos-amprenavir, imatinib and verapamil. In the above U.S. Food and Drug Administration guidelines, among the "drug that inhibits CYP2C8", gemfibrozil is listed as a potent CYP2C8 inhibitor. In the above U.S. Food and Drug Administration guidelines, among the "drug that inhibits CYP2C9," amiodarone, fluconazole, miconazole, and oxandrolone are listed as moderate CYP2C9 inhibitors.

In the present invention, "rifampicin" includes, not only rifampicin itself, but also a pharmaceutically acceptable salt thereof, and a solvate of rifampicin or its pharmaceutically acceptable salt with water and the like. In one embodiment of the present invention, rifampicin is rifampicin as listed in the Japanese Pharmacopoeia, Seventeenth Edition.

In the present specification, "clarithromycin" includes not only clarithromycin itself, but also a pharmaceutically acceptable salt thereof, a solvate of clarithromycin or its pharmaceutically acceptable salt with water and the like. In one embodiment of the present invention, clarithromycin is clarithromycin as listed in the Japanese Pharmacopoeia, Seventeenth Edition.

In the present specification, "cyclosporine" includes not only cyclosporine A represented by the following formula (4); but also cyclosporine B, cyclosporine C, cyclosporine D, cyclosporine E, cyclosporine F, cyclosporine G, and cyclosporine H, which are analogs of cyclosporine A; a pharmaceutically acceptable salt of cyclosporine; and a solvate of cyclosporine or its pharmaceutically acceptable salt with water and the like.

[Formula 4]

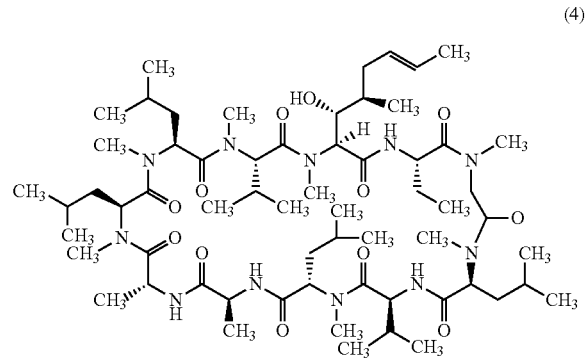

(4)

In one embodiment of the present invention, cyclosporine is cyclosporine A, preferably cyclosporine listed in the Japanese Pharmacopeia, Seventeenth Edition (cyclosporine A).

In the present invention, "clopidogrel" includes, not only clopidogrel itself, but also a pharmaceutically acceptable salt thereof, and a solvate of clopidogrel or its pharmaceutically acceptable salt with water and the like. Examples of salt of clopidogrel include, but are not limited to, a hydrochloride, a sulfate, a bisulfate, a hydrobromide, and a taurocholate. In one embodiment of the present invention, clopidogrel is clopidogrel sulfate, preferably clopidogrel sulfate as listed in the Japanese Pharmacopoeia, Seventeenth Edition.

In the present invention, "a patient in need of pemafibrate therapy" or "a patient in need of treatment with pemafibrate, a salt thereof, or a solvate of any of these" includes, but not limited to, a patient expressing one or more diseases selected from the group consisting of, for example, hyperlipidemia, dyslipidemia, arteriosclerosis, diabetes mellitus, diabetic complications, inflammation, non-alcoholic steatohepatitis, primary biliary cirrhosis, and heart disease.

In the present invention, "treatment with an OATP1B inhibitor" refers to administration of an OATP1B inhibitor for the treatment of a disease, and the OATP1B inhibitor used can differ depending on the disease to be treated. For example, rifampicin is used in the treatment of pulmonary tuberculosis and other tuberculosis, non-tuberculous mycobacteriosis, including *Mycobacterium avium* complex (MAC) disease, and leprosy. Clarithromycin is used for the treatment of general infectious diseases (superficial skin infections, deep skin infections, lymphangitis, lymphadenitis, chronic pyoderma, secondary infections caused by trauma, burns and surgical wounds, perianal abscess, pharyngeal/laryngitis, tonsillitis, acute bronchitis, pneumonia, lung abscess, secondary infection of chronic respiratory lesions, urethritis, cervicitis, infectious enteritis, otitis media, sinusitis, periodontitis, pericoronitis, or jaw inflammation by one or more bacteria selected from the group consisting of *Staphylococcus, Streptococcus, Streptococcus pneumoniae, Moraxella* (Branhamera) *catarrhalis, Haemophilus influenzae, Legionella, Campylobacter, Peptostreptococcus, Chlamydia*, and *Mycoplasma*), nontuberculous mycobacterial disease including *Mycobacterium avium* complex (MAC) disease and *Helicobacter pylori* infection. Cyclosporine reduces rejection in organ transplantation (kidney, liver, heart, lung, pancreas, small intestine), rejection in bone marrow transplantation and graft-versus-host disease, Behcet's disease (if ocular symptoms are present) and other noninfectious uveitis (limited to active intermediate or posterior noninfectious uveitis that may be ineffective with existing therapy), psoriasis (psoriasis vulgaris (if skin rash is more than 30% of the whole body or refractory), pustular psoriasis, erythrodermic psoriasis, arthritic psoriasis), anemia (aplastic anemia (severe), pure red cell aplasia), nephrotic syndrome (frequent relapsing, or with resistance in steroid), myasthenia gravis (in the treatment after thymectomy, when the effect of steroids is insufficient or when it is difficult to administer steroids due to adverse reactions). It is also used for the treatment of atopic dermatitis (patients who are unable to achieve a satisfactory effect with existing treatments). Clopidogrel is used to suppress recurrence after ischemic cerebrovascular disorder (excluding cardiogenic cerebrovascular embolism), to treat ischemic heart disease to which percutaneous coronary intervention (PCI) is applied (acute coronary syndrome (unstable angina pectoris, non-ST-elevation myocardial infarction, ST-elevation myocardial infarction), stable angina pectoris, old myocardial infarction), and to suppress thrombus and embolus formation in peripheral arterial disease. However, treatment with an OATP1B inhibitor is not limited to the treatment of these diseases.

In one embodiment of the present invention, the patient in need of pemafibrate therapy is a patient in need of further treatment with an OATP1B inhibitor. Such patients include, a patient in need of additional pemafibrate therapy during treatment with an OATP1B inhibitor, a patient in need of additional therapy with an OATP1B inhibitor during pemafibrate therapy, and a patient in need of simultaneous start of pemafibrate therapy and treatment with an OATP1B inhibitor.

In the present invention, "treatment with a CYP inhibitor" refers to administration of a CYP inhibitor for the treatment of a disease, and the CYP inhibitor to be used depends on the disease to be treated. For example, clarithromycin is used for the treatment of general infectious diseases (superficial skin infections, deep skin infections, lymphangitis, lymphadenitis, chronic pyoderma, secondary infections caused by trauma, burns and surgical wounds, perianal abscess, pharyngeal/laryngitis, tonsillitis, acute bronchitis, pneumonia lung abscess, secondary infection of chronic respiratory lesions, urethritis, cervicitis, infectious enteritis, otitis media, sinusitis, periodontitis, pericoronitis, or jaw inflammation by one or more bacteria selected from the group consisting of *Staphylococcus, Streptococcus, Streptococcus pneumoniae, Moraxella* (Branhamera) *catarrhalis, Haemophilus influenzae, Legionella, Campylobacter, Peptostreptococcus, Chlamydia*, and *Mycoplasma*), nontuberculous mycobacterial disease including *Mycobacterium avium* complex (MAC) disease and *Helicobacter pylori* infection. Cyclosporine reduces rejection in organ transplantation (kidney, liver, heart, lung, pancreas, small intestine), rejection in bone marrow transplantation and graft-versus-host disease, Behcet's disease (if ocular symptoms are present) and other noninfectious uveitis (limited to active intermediate or posterior noninfectious uveitis that may be ineffective with existing therapy), psoriasis (psoriasis vulgaris (if skin rash is more than 30% of the whole body or refractory), pustular psoriasis, erythrodermic psoriasis, arthritic psoriasis), anemia (if erythroderma, arthritic psoriasis), (aplastic anemia (severe), pure red cell aplasia), nephrotic syndrome (frequent relapsing, or with resistance in steroid), myasthenia gravis (in the treatment after thymectomy, when the effect of steroids is insufficient or when it is difficult to administer steroids due to adverse reactions). It is also used for the treatment of atopic dermatitis (patients who are unable to achieve a satisfactory effect with existing treatments). Clopidogrel is used to suppress recurrence after ischemic cerebrovascular disorder (excluding cardiogenic cerebrovascular embolism), to treat ischemic heart disease to which percutaneous coronary angioplasty (PCI) is applied (acute coronary syndrome (unstable angina pectoris, non-ST-elevation myocardial infarction, ST-elevation myocardial infarction), stable angina pectoris, old myocardial infarction), and to suppress thrombus and embolus formation in peripheral arterial diseases. However, treatment with a CYP inhibitor is not limited to the treatment of these diseases.

In one embodiment of the present invention, the patient in need of pemafibrate therapy is a patient in need of further treatment with a CYP inhibitor. Such patients include, for example, a patient in need of further pemafibrate therapy during treatment with a CYP inhibitor, a patient in need of additional treatment with a CYP inhibitor during pemafibrate therapy, and a patient in need of simultaneous start of pemafibrate therapy and treatment with a CYP inhibitor.

In the present invent ion, a "concomitant use" ref ere to a patient's taking two or more medicaments or to let a patient take two or more medicaments. In one embodiment of the present invention, when the patient takes two medicaments, for example, the patient may take two medications simultaneously or one by one at an interval.

Investigations by the present inventors revealed that the plasma concentration of pemafibrate were increased when pemafibrate, a salt thereof, or a solvate of any of these was used concomitant with rifampicin, as compared with administration of pemafibrate, a salt thereof, or a solvate of any of these alone (see Examples below). Such an increase in plasma concentration of pemafibrate may cause unexpected side effects. Therefore, in the present invention, in order to suppress such an increase in plasma concentration of pemafibrate, the concomitant use is avoided or suspended, or the dose of pemafibrate, a salt thereof, or a solvate of any of these is reduced.

Rifampicin is a drug known to act as an inhibitor of OATP1B1 and OATP1B3 by a single administration, and it is conceivable that its inhibitory effect is involved in increasing plasma concentration of pemafibrate. That is, concomitant use of an OATP1B inhibitor with pemafibrate, a salt thereof, or a solvate of any of these may increase plasma concentration of pemafibrate. Therefore, in order to suppress the increase in the plasma concentration of pemafibrate, the concomitant use was avoided or suspended, or the dose of pemafibrate, a salt thereof, or a solvate of any of these was reduced.

Clarithromycin is known to inhibit CYP3A, OATP1B1, and OATP1B3, thereby causing drug interactions, and may be involved in increasing plasma concentration of pemafibrate. That is, if the drug inhibits CYP3A, OATP1B1, and OATP1B3, the plasma concentration of pemafibrate may be increased by concomitant use of pemafibrate, a salt thereof, or a solvate of any of these. Therefore, in order to suppress the increase in the plasma concentration of pemafibrate, the concomitant use was avoided or suspended, or the dose of pemafibrate, a salt thereof, or a solvate of any of these was reduced.

In the present invention, examples of "a drug that inhibits CYP3A, OATP1B1, and OATP1B3" include clarithromycin, cyclosporine, and HIV-protease inhibitors. Examples of HIV protease inhibitors include atazanavir, a salt thereof, or a solvate of any of these (atazanavir sulfate etc.), indinavir, a salt thereof, or a solvate of any of these (indinavir sulfate ethanol adduct etc.), saquinavir, a salt thereof, or a solvate of any of these (saquinavir mesylate etc.), darnavir, a salt thereof, or a solvate of any of these (darnavir ethanol adduct etc.), nelfinavir, a salt thereof, or a solvate of any of these (nelfinavir mesylate etc.), phosamprenavir, a salt thereof, or a solvate of any of these (phosamprenavir calcium hydrate etc.), ritonavir, a salt thereof, or a solvate of any of these or a solvate, and lopinavir, a salt thereof, or a solvate of any of these, and in particular ritonavir, a salt thereof, or a solvate of any of these, are known to inhibit CYP3A, OATP1B1 and OATP1B3.

In one embodiment of the present invention, "a medicament comprising a drug that inhibits CYP3A, OATP1B1, and OATP1B3" includes a concomitant drug that exhibits other pharmacological action than a medicament that includes either clarithromycin, cyclosporine, or an HIV-protease inhibitor as the sole pharmacological action compound. The above combination agents include a combination agent of ritonavir and lopinavir (e.g., Kaletra), a combination agent of ritonavir and ombitavir hydrate and palitaprevir hydrate (VIEKIRAX), a combination agent of ritonavir and darnavir ethanol adduct, and a combination agent of darnavir ethanol adduct and cobicistat (Prezcobix).

Concomitant use of "a drug that inhibits CYP3A" and "a drug that inhibits OATP1B1 and OATP1B3" may inhibit CYP3A, OATP1B1, and OATP1B3, and may increase plasma concentration of pemafibrate by administering pemafibrate, a salt thereof, or a solvate of any of these to the same patients. Therefore, caution should be exercised when pemafibrate, a salt thereof, or a solvate of any of these is used concomitant with "a drug that inhibits CYP3A" or "a drug that inhibits OATP1B1 and OATP1B3," and avoiding or suspending the concomitant use, or reducing the dose of pemafibrate, a salt thereof, or a solvate of any of these can suppress the increase in plasma concentration of pemafibrate.

Cyclosporine is also known to inhibit CYP3A, CYP2C8, CYP2C9, OATP1B1, and OATP1B3, and to cause drug interactions, and it is considered that cyclosporine is involved in increasing plasma concentration of pemafibrate. That is, if a drug inhibits CYP3A, CYP2C8, CYP2C9, OATP1B1, and OATP1B3, plasma concentration of pemafibrate may be increased by concomitant use of pemafibrate, a salt thereof, or a solvate of any of these with such a drug. Therefore, in order to suppress the increase in the plasma concentration of pemafibrate, the present inventors determined to avoid or suspend the concomitant use, or reduce the dose of pemafibrate, a salt thereof, or a solvate of any of these.

In addition, concomitant use of "a drug that inhibits CYP3A", "a drug that inhibits CYP2C8", "a drug that inhibits CYP2C9", and "a drug that inhibits OATP1B1 and OATP1B3" may inhibit CYP3A, CYP2C8, CYP2C9, OATP1B1 and OATP1B3, and may increase the plasma concentration of pemafibrate by administering pemafibrate, a salt thereof, or a solvate of any of these to the same subject. Therefore, care must be taken when pemafibrate, a salt thereof, or a solvate of any of these is concomitantly used with one or more drugs selected from the group consisting of "a drug that inhibits CYP3A", "a drug that inhibits CYP2C8", "a drug that inhibits CYP2C9" and "a drug that inhibits OATP1B1 and OATP1B3". Increase in the plasma concentration of pemafibrate can be suppressed by avoiding or suspending the concomitant use or by reducing the dose of pemafibrate, a salt thereof, or a solvate of any of these.

Clopidogrel is also known to inhibit CYP2C8 and OATP1B1 and cause drug interactions, and may be involved in increasing plasma concentration of pemafibrate. That is, if the drug inhibits CYP2C8 and OATP1B1, the plasma concentration of pemafibrate may be increased by concomitant use with pemafibrate, a salt thereof, or a solvate of any of these or solvates thereof. Therefore, in order to suppress an increase in the plasma concentration of pemafibrate, the present inventors determined to avoid or suspend the concomitant use, or to reduce the dose of pemafibrate, a salt thereof, or a solvate of any of these.

In addition, concomitant use of "a drug that inhibits CYP2C8" with "a drug that inhibits OATP1B1" may inhibit CYP2C8 and OATP1B1, and if pemafibrate, a salt thereof, or a solvate of any of these is further administered to the same patients, the plasma concentration of pemafibrate may be increased. Therefore, caution should be exercised when using pemafibrate, a salt thereof, or a solvate of any of these concomitant with "a drug that inhibits CYP2C8" or "a drug that inhibits OATP1B1", and avoidance or suspension of such concomitant use or reduction of pemafibrate, a salt thereof, or a solvate of any of these can suppress an increase in plasma concentration of pemafibrate.

In the present specification, the "step of avoiding or suspending the concomitant use with the pharmaceutical containing the OATP1B inhibitor" is not particularly limited, and includes, for example, any one of the following steps (i) to (vii).

(i) Recommending a patient to contraindicate the use of pemafibrate, a salt thereof, or a solvate of any of these concomitant with a drug containing an OATP1B inhibitor because of increased plasma concentration of pemafibrate.

(ii) Recommending a patient to avoid or discontinue concomitant use of pemafibrate, a salt thereof, or a solvate of any of these with a medicament containing an OATP1B inhibitor because of increased plasma concentration of pemafibrate.

(iii) Recommending the subject that the use of a medicament containing an OATP1B inhibitor should be suspended prior to the use of a medicament containing pemafibrate, a salt thereof, or a solvate of any of these.

(iv) Recommending a patient to contraindicate concomitant use of pemafibrate, a salt thereof, or a solvate of any of these with a medicament containing an OATP1B inhibitor because of increased plasma concentration of pemafibrate.

(v) Recommending a patient to avoid or discontinue concomitant use of pemafibrate, a salt thereof, or a solvate of any of these with a medicament containing an OATP1B inhibitor because of increased plasma concentration of pemafibrate in principle.

(vi) Recommending a patient to administer a medication containing pemafibrate, a salt thereof, or a solvate of any of these with caution against the onset of adverse reactions, because the plasma concentration of pemafibrate are increased by concomitantly administering it with a medication containing an OATP1B inhibitor. Recommending patients to administer a medication containing pemafibrate, a salt thereof, or a solvate of any of these with caution against the onset of adverse reactions.

(vii) Any one of the steps selected from the group consisting of (i) to (vi) which is carried out after explaining to the patient that the normal metabolism of pemafibrate, a salt thereof, or a solvate of any of these is inhibited by taking a medicament comprising an OATP1B inhibitor.

The above (i) to (vii) can replace the "OATP1B inhibitor" with any drug, and can be read as a step for an arbitrary drug. The arbitrary drug is one or more drugs selected from the group consisting of, for example, but not limited to, a CYP inhibitor, a drug that inhibits CYP3A, a drug that inhibits CYP2C8, a drug that inhibits CYP2C9, a drug that inhibits OATP1B1 and OATP1B3, and a drug that inhibits OATP1B1.

In the present invention, "dose" means an amount of active ingredient used per day and is expressed in units of g/day or mg/day. In one embodiment of the present invention, the dose of pemafibrate, a salt thereof, or a solvate of any of these to a patient in need of pemafibrate therapy is preferably 0.1 to 0.4 mg/day. If the patient further requires treatment with an OATP1B inhibitor, less than 0.4 mg/day is preferable, and 0.1 to 0.2 mg/day is more preferable. In one embodiment of the present invention, when pemafibrate is used concomitantly with clarithromycin or clopidogrel, it is preferable that the daily dose of pemafibrate be 0.1 mg and the maximal dose be up to 0.2 mg per day, but the dose is not limited thereto. It is also preferable that pemafibrate, a salt thereof, or a solvate of any of these be administered in a manner that the above daily dose is divided into twice.

In the present invention, "a step of reducing the dose of pemafibrate, a salt thereof, or a solvate of any of these" means changing the dose of pemafibrate, a salt thereof, or a solvate of any of these selected from the group consisting of from 0.4 mg/day to 0.35 mg/day, from 0.4 mg/day to 0.3 mg/day, from 0.4 mg/day to 0.25 mg/day, from 0.4 mg/day to 0.2 mg/day, from 0.4 mg/day to 0.15 mg/day, from 0.4 mg/day to 0.1 mg/day, from 0.4 mg/day to 0.05 mg/day, from 0.35 mg/day to 0.3 mg/day, from 0.35 mg/day to 0.25 mg/day, and from 0.35 mg/day to 0.2 mg/day, and from 0.35 mg/day to 0.15 mg/day, from 0.35 mg/day to 0.1 mg/day, from 0.35 mg/day to 0.05 mg/day, from 0.3 mg/day to 0.25 mg/day, from 0.3 mg/day to 0.2 mg/day, from 0.3 mg/day to 0.15 mg/day, from 0.3 mg/day to 0.05 mg/day, from 0.25 mg/day to 0.2 mg/day, from 0.25 mg/day to 0.15 mg/day, 0.25 mg/day to 0.1 mg/day, from 0.25 mg/day to 0.05 mg/day, from 0.2 mg/day to 0.15 mg/day, from 0.2 mg/day to 0.1 mg/day, from 0.2 mg/day to 0.05 mg/day, from 0.15 mg/day to 0.1 mg/day, from 0.15 mg/day to 0.05 mg/day, and from 0.1 mg/day to 0.05 mg/day. Among these, it is preferable to reduce the dose of pemafibrate, a salt thereof, or a solvate of any of these, compared with the dose when pemafibrate is administered alone, to ½ or less.

In the present invention, "reducing the dose of pemafibrate, a salt thereof, or a solvate of any of these" can be expressed, for example, as "reducing the amount of pemafibrate, a salt thereof, or a solvate of any of these to be administered", "reducing the amount of pemafibrate, a salt thereof, or a solvate of any of these" or "lowering the dose of pemafibrate, a salt thereof, or a solvate of any of these."

In another embodiment of the present invention, the "step of avoiding or suspending concomitant use" and the "step of reducing the dose of pemafibrate, a salt thereof, or a solvate of any of these" for suppressing an increase in plasma concentration of pemafibrate can be performed as required, and embodiments thereof include, for example, the medicaments recited in [47] and [49], the pharmaceutical kits recited in [48] and [50], the methods for treatment recited in [52] and [56], and the use for treatment recited in [54] and [58], and the like.

In one embodiment of the present invention, the dose of clarithromycin to a patient in need of treatment with clarithromycin is preferably from 200 to 1,600 mg/day, preferably 200 to 800 mg/day for the treatment of general infectious diseases, 400 to 1,600 mg/day for the treatment of non-tuberculous mycobacteriosis, and 200 to 800 mg/day for the treatment of *Helicobacter pylori* infections.

In one embodiment of the present invention, the dose of clopidogrel, a salt thereof, or a solvate of any of these to a patient in need of treatment with clopidogrel, a salt thereof, or a solvate of any of these is 75 to 400 mg/day, preferably 75 to 300 mg/day as clopidogrel, more preferably 391.5 mg/day of clopidogrel sulfate (equivalent to 300 mg/day of clopidogrel) on day 1 and 97.875 mg/day of clopidogrel sulfate (equivalent to 75 mg/day of clopidogrel) on and after day 2 of administration.

One embodiment of the present invention includes a pharmaceutical kit comprising (A) a medicament comprising pemafibrate, a salt thereof, or a solvate of any of these or solvate thereof as an active ingredient; and (B) an instruction to avoid or suspend concomitant use of the (A) and a medicament comprising an OATP1B inhibitor or to reduce the dose of pemafibrate, a salt thereof, or a solvate of any of these.

In this specification, "an instruction to avoid or suspend concomitant use" is an instruction describing a situation in which concomitant use of two specific medicaments should be avoided or suspended. In one embodiment of the present invention, the "instruction to avoid or suspend concomitant use of Medicament A and Medicament B" is not particularly limited, but includes, for example, an instruction for instructing (a) to (h) below.

(a) Do not administer Medicament B to a patient receiving Medicament A.

(b) Do not concomitantly use Medicament A and Medicament B (c) In principle, Medicament A should not be administered to a patient receiving Medicament B, but should be administered with care when particularly necessary.

(d) In principle, Medicament A and Medicament B should not be used concomitantly, but concomitant use should be made with caution only when it is judged that the concomitant use is unavoidable for treatment.

(e) Caution should be exercised when administering Medicament A to a patient receiving Medicament B.

(f) Caution should be exercised when Medicament A and Medicament B are used concomitantly.

(g) If the patient is taking Medicament B, suspend taking medicament B before using Medicament A.

(h) If the patient is taking Medicament B, explain the current compliance status to the physician or pharmacist before using Medicament A.

In the present invention, "instruction" include a package insert, a package label, or a user manual, and include, but are not limited to, a package insert, an interview form, a prescribing information, a patient information leaflet, for example.

The following examples and test example are given to explain the present invention in more detail, but the present invention is not limited thereto.

EXAMPLES

Example 1: Drug Interaction Study of Pemafibrate with Rifampicin

A study was conducted to investigate the effect of rifampicin on the pharmacokinetics of pemafibrate in healthy adult subjects.
[Subject]
20 healthy adults
[Dose and Administration]
Subjects were orally administered on the following schedule. The administration of 0.4 mg of pemafibrate on Days 1 and 4 was carried out under fasting for at least 8 hours, and the fasting was maintained for 4 hours after the administration.
  Day 1: Pemafibrate 0.4 mg alone
  Day 4: A single dose of 0.4 mg of pemafibrate plus 600 mg of rifampicin
  Days 5-6: Rifampicin 600 mg alone
(Measurement)

Plasma concentration of pemafibrate was measured on blood samples from patients taken prior to and at 0.25, 0.5, 1, 1.5, 2, 3, 4, 6, 8, 10, 12, 14, 16, 24, 36, 48, 72 hours after administration of the drug on Days 1 and 4.

For estimates of the $C_{max}$ of pemafibrate and the area under the concentration-time curves ($AUC_{0\text{-}inf}$) up to infinity hours, the geometric mean values and the ratios of the geometric mean values for concomitant administration to those for the single administration are shown in Table 1. As can be seen from Table 1, concomitant administration of pemafibrate and rifampicin resulted in an increase in the plasma concentration of pemafibrate compared with administration of pemafibrate alone.

TABLE 1

| Parameter | Single administration | Concomitant administration | Ratio (concomitant use/single use) 90% confidence interval |
|---|---|---|---|
| Cmax (ng/mL) | 5.672 | 53.512 | 9.4336<br>8.3626-10.6419 |
| $AUC_{0\text{-}inf}$ (ng · h/mL) | 20.069 | 218.774 | 10.9009<br>9.9154-11.9844 |

Example 2: Drug Interaction Study of Pemafibrate with Clarithromycin

A study was conducted to investigate the effect of clarithromycin on the pharmacokinetics of pemafibrate in healthy adult subjects.
[Subject]
20 healthy adult subjects
[Dose and Administration]
Subjects were orally administered on the following schedule. The administration of 0.4 mg of pemafibrate on Days 1 and 9 was carried out under fasting for at least 8 hours, and the fasting was maintained for 4 hours after the administration.
  Day 1: Pemafibrate 0.4 mg alone
  Day 4 to 8: Clarithromycin 500 mg twice per day (1000 mg/day)
  Day 9: Pemafibrate 0.4 mg single dose and Clarithromycin 500 mg twice per day (1000 mg/day)
  Day 10 to 11: Clarithromycin 500 mg twice per day (1000 mg/day)
Measurement Plasma concentration of pemafibrate was measured on blood samples from patients collected prior to and at 0.25, 0.5, 1, 1.5, 2, 3, 4, 6, 8, 10, 12, 14, 16, 24, 36, 48, 72 hours after administration of 0.4 mg of pemafibrate on Days 1 and 9.

For estimates of the $C_{max}$ of pemafibrate and the area under the concentration-time curves ($AUC_{0\text{-}inf}$) up to infinity hours, the geometric mean values and the ratios of the geometric mean values for concomitant administration to those for the single administration are shown in Table 2. As can be seen from Table 2, concomitant administration of pemafibrate and clarithromycin resulted in an increase in the plasma concentration of pemafibrate compared with administration of pemafibrate alone.

TABLE 2

| Parameter | Single administration | Concomitant administration | Ratio (concomitant use/single use) 90% confidence interval |
|---|---|---|---|
| Cmax (ng/mL) | 4.673 | 11.331 | 2.4246<br>2.1632-2.7174 |
| $AUC_{0\text{-}inf}$ (ng · h/mL) | 17.006 | 35.670 | 2.0975<br>1.9158-2.2964 |

Example 3: Drug Interaction Study of Pemafibrate with Cyclosporine

A study was conducted to investigate the effect of cyclosporine on the pharmacokinetics of pemafibrate in healthy adult subjects.
[Subject]
20 healthy adults
[Dose and Administration]
Subjects were orally administered on the following schedule. Drug administration was carried out under fasting for at least 8 hours, and fasting was maintained for 4 hours after administration.
  Day 1: Pemafibrate 0.4 mg alone
  Day 4: Combined single dose of 0.4 mg of pemafibrate and 600 mg of cyclosporine (Neoral® or its equivalent)
[Measurement]

Plasma concentration of pemafibrate was measured on blood samples from patients taken prior to and at 0.25, 0.5, 1, 1.5, 2, 3, 4, 6, 8, 10, 12, 14, 16, 24, 36, 48, 72 hours after administration of the drug on Days 1 and 4.

For estimates of the $C_{max}$ of pemafibrate and the area under the concentration-time curves ($AUC_{0\text{-}inf}$) up to infinity hours, the geometric mean values and the ratios of the geometric mean values for concomitant administration to those for the single administration are shown in Table 3. As can be seen from Table 3, concomitant administration of pemafibrate and cyclosporine resulted in an increase in the plasma concentration of pemafibrate compared with administration of pemafibrate alone.

TABLE 3

| Parameter | Single administration | Concomitant administration | Ratio (concomitant use/single use) 90% confidence interval |
|---|---|---|---|
| Cmax (ng/mL) | 4.593 | 41.175 | 8.9644 7.5151-10.6931 |
| $AUC_{0\text{-}inf}$ (ng · h/mL) | 13.388 | 187.363 | 13.9947 12.6175-15.5223 |

Example 4: Drug Interaction Study of Pemafibrate with Clopidogrel

A study was conducted to investigate the effect of clopidogrel on the pharmacokinetics of pemafibrate in healthy adult subjects.
[Subject]
20 healthy adults
[Dose and Administration]
Subjects were orally administered on the following schedule. Pemafibrate administration on Days 1, 4, and 7 was carried out under fasting for at least 8 hours and maintained fasting for 4 hours after administration.
  Day 1: Pemafibrate 0.4 mg alone
  Day 4: A single dose of 0.4 mg of pemafibrate plus 391.5 mg of clopidogrel sulfate (equivalent to 300 mg of clopidogrel)
  Day 5 to 6: Clopidogrel Sulfate 91.875 mg (equivalent to Clopidogrel 75 mg) alone
  Day 7: A single dose of 0.4 mg of pemafibrate and 91.875 mg of clopidogrel sulfate (equivalent to 75 mg of clopidogrel)
  Day 8 to 9: Clopidogrel Sulfate 91.875 mg (equivalent to Clopidogrel 75 mg) alone
Measurement
Plasma concentration of pemafibrate was measured on blood samples from patients taken prior to and at 0.25, 0.5, 1, 1.5, 2, 3, 4, 6, 8, 10, 12, 14, 16, 24, 36, 48, 72 hours after administration of the drug on Days 1, 4, and 7.

For estimates of the $C_{max}$ of pemafibrate and the area under the concentration-time curves ($AUC_{0\text{-}inf}$) up to infinity hours, the geometric mean values and the ratios of the geometric mean values of the single-dose concomitant administration (Day 4) to those for the single administration (Day 1) are shown in Table 4. As can be seen from Table 4, concomitant administration of pemafibrate and clopidogrel resulted in an increase in the plasma concentration of pemafibrate compared with administration of pemafibrate alone.

TABLE 4

| Parameter | Single administration | Concomitant administration | Ratio (concomitant use/single use) 90% confidence interval |
|---|---|---|---|
| Cmax (ng/mL) | 4.7661 | 7.0799 | 1.4855 1.3915-1.5858 |
| $AUC_{0\text{-}inf}$ (ng · h/mL) | 16.0763 | 38.1452 | 2.3728 2.2473-2.5052 |

For the $C_{max}$ and $AUC_{0\text{-}inf}$ of pemafibrate, the geometric mean values and the ratios of the geometric mean values for concomitant administration after repeated administration of clopidogrel (day 7) to those for the single administration (day 1) are shown in Table 5. As can be seen from Table 5, concomitant administration of pemafibrate and clopidogrel resulted in an increase in the plasma concentration of pemafibrate compared with administration of pemafibrate alone.

TABLE 5

| Parameter | Single administration | Concomitant administration | Ratio (concomitant use/single use) 90% confidence interval |
|---|---|---|---|
| Cmax (ng/mL) | 4.7661 | 6.3935 | 1.3415 1.2583-1.4302 |
| $AUC_{0\text{-}inf}$ (ng · h/mL) | 16.0763 | 33.5611 | 2.0876 1.9811-2.1998 |

INDUSTRIAL APPLICABILITY

The present invention can avoid an increase in plasma concentration of pemafibrate, a salt thereof, or a solvate of any of these. Thus, a medicament can be provided for the effective and safe use of pemafibrate, a salt thereof, or a solvate of any of these.

The invention claimed is:
1. A method of treating dyslipidemia in a patient who is taking an original daily dose of 0.4 mg per day of pemafibrate or a pharmaceutically acceptable salt thereof, comprising the steps of:
   i) administering rifampin to the patient; and
   ii) eliminating any administration of pemafibrate or a pharmaceutically acceptable salt thereof to the patient.
2. The method of claim 1, comprising administering 600 mg/day rifampin.
3. The method of claim 1, further comprising, after step (ii), eliminating any administration of rifampin to the patient, and resuming the original daily dose.
4. A method of treating dyslipidemia in a patient who is taking an original daily dose of 0.4 mg per day of pemafibrate or a pharmaceutically acceptable salt thereof, comprising the steps of:
   i) administering cyclosporin to the patient; and
   ii) eliminating any administration of pemafibrate or a pharmaceutically acceptable salt thereof to the patient.
5. The method of claim 4, comprising administering 600 mg/day cyclosporin.
6. The method of claim 4, further comprising, after step (ii), eliminating any administration of cyclosporin to the patient, and resuming the original daily dose.

\* \* \* \* \*